United States Patent [19]

Oja et al.

[11] Patent Number: 4,497,208

[45] Date of Patent: Feb. 5, 1985

[54] MEASUREMENT OF ELECTRO-KINETIC PROPERTIES OF A SOLUTION

[75] Inventors: Tõnis Oja, Scarsdale, N.Y.; Gary L. Petersen, Kingstown, R.I.; David W. Cannon, Attleboro Falls, Mass.

[73] Assignee: Matec, Inc., Warwick, R.I.

[21] Appl. No.: 507,111

[22] Filed: Jun. 23, 1983

[51] Int. Cl.³ .............................................. G01N 29/00
[52] U.S. Cl. .................................... 73/584; 73/61 R; 73/63; 73/590
[58] Field of Search ..................... 73/61 R, 61.1 R, 63, 73/599, 597, 584, 590; 162/192, 198

[56] References Cited

U.S. PATENT DOCUMENTS 3,710,615  1/1973  Johnson et al. ..................... 73/61 R
3,774,717  11/1973 Chodorow ............................ 73/599
4,294,656  10/1981 Beck et al. .......................... 162/192

OTHER PUBLICATIONS

Beck et al., (*Tappi*, vol. 61, pp. 63–65) Sep. 1978, "Measuring Zeta Potential by Ultrasonic Waves".
Debye, (Journal Chemical Physics, vol. I, p. 13, 1933), "A Method for the Determination of the Mass of Electrolytic Ions".
Borsay et al. (J. Acoust. Soc. Am. vol. 64, pp. 240–242, 1978), "Generation of Ultrasound at Metal–Electrolyte Interfaces".

*Primary Examiner*—Stephen A. Kreitman
*Attorney, Agent, or Firm*—Barlow & Barlow Ltd.

[57] ABSTRACT

This invention is concerned with a method and apparatus for measuring the electro-kinetic properties of a liquid which may be a mixture such as a slurry of particles, or a dispersion of droplets. Electrodes are placed in the liquid and an apparatus is provided for applying an alternating electrical potential to these electrodes. The electric field from this alternating potential acts upon the charged elements in the liquid, resulting in the generation of sound at the frequency of the applied electrical potential. By placing a conventional acoustic transducer in a spaced relationship to the electrodes, the acoustic signal is detected and measured. The amplitude of the acoustical signal will be a function of the electro-kinetic properties of the particles or emulsion droplets in the liquid. In its preferred form, the electrodes that are placed in the liquid have a spacial separation of one-half wave length, or odd integer multiples of half wave length of the sound which they generate. Coupled to the receiving transducer is a receiver that will amplify the signal to convenient levels. With this device a wide range of electro-kinetic measurements become possible even in highly concentrated systems.

9 Claims, 4 Drawing Figures

MEASUREMENT OF ELECTRO-KINETIC PROPERTIES OF A SOLUTION

BACKGROUND OF THE INVENTION

In the prior art it has been proposed to test materials and to excite solutions and slurries with the use of ultrasonic energy. Slurries are defined as one phase (liquid or solid) dispersed in another liquid phase such as oil droplets in water or coal particles in methanol. In essence, whether it is in connection with a solid material, a liquid solution, or slurry, it is common to send ultrasonic pulses from a transducer, that usually takes the form of a crystal such as a barium titanate, lead zirconate titanate, lithium niobate etc., into the object being tested. In some instances, the same crystal acts as a receiver and detects the acoustic echoes that might reverberate from the test material. In some cases, moving fluids have been studied using these methods. However, practical measurements using these techniques have been limited to acoustic attenuation and velocity.

In 1933 P. Debye, (Journal Chemical Physics, Vol. I, Pg. 13, 1933), predicted that when sound is propagated in an ionic solution, a momentary charge separation occurs because of the different ionic mobilities. This predicted effect occurs if cations and anions of an electrolyte have different effective masses and frictional co-efficients. This momentary charge separation, where one region will be charged positively with respect to an adjacent negatively charged region implies than an instantaneous electrical signal can be measured. Thus, if inert metal probes are placed in two different regions, a potential will be observed with the same frequency as the sound wave. A similar effect arises for colloidal particles and emulsion droplets because of the distortion of their ionic surroundings. This concept was first predicted by A. Rutgers in 1938 (Physica 5:46) and observed further by E. Yeager in 1949 (Journal Chemical Physics, Vol. 17, Page 411). The modern method for measuring the electrical potential in colloidal systems is given by U. Beck et al (TAPPI Vol. 61, Pages 63–65), and a further arrangement for ionic solutions is seen in Borsay et al (Journal of the Acoustical Society of America, Pages, 240–242, Vol. 64, July, 1978). In all of the prior experiments, difficulty has been encountered in the fact that the voltage being measured is quite small, and depends on the sound amplitude at the electrodes and the electrical conductiviy of the liquid. It is desirable therefore to improve upon the system for measuring the electrical potential, predicted by Debye. This potential has been termed "The Ultrasonic Vibrational Potential" (U.V.P.) and is closely related to the concept of zeta potential. We have, therefore, used the inverse effect from the one described by Debye, that is to say the sound is generated by an electric field, in a practical device to study liquids.

SUMMARY OF THE INVENTION

In accordance with the present invention, a method and apparatus for developing ultrasonic waves in a solution or suspension is disclosed. The signal emitting device which is used consists essentially of an electrode pair, one member of which may be a ground plane, immersed in the liquid, which is energized electrically by means of continuous or pulsed alternating electrical potential. Essentially any configuration which is in contact with the liquid may be used; however, the direction and amplitude of the sound will be affected by the geometry of this configuration. The liquid into which the device is inserted may be either standing or continuously flowing. Acoustic energy will be developed, due to the displacement of the cations and anions, caused by the electric field at the frequency that is applied to the device. The amplitude of the acoustic wave produced will depend on the number per-unit volume of suspended objects, such as colloid particles or emulsion droplets, and the amount of charge per particle or droplet. Essentially, therefore, the invention involves a method of measuring the electro-kinetic properties of a particle dispersion where electrodes are placed in a dispersion, and these electrodes are energized with an alternating electric potential which causes a charge displacement in the solution at the frequency of alternating electric potential. The instrumentation holds the amplitudes of the potential applied to the electrodes constant, and a conventional acoustic receiver transducer that is spaced some distance from the electrodes is used to detect the acoustical signal developed within the liquid. Holding the electric potential amplitude constant compensates for changes in the conductivity or electric impedance of the liquid, and represents one of the principle advantages of generating the sound wave with an electric field rather than detecting the sound with the electric field. Separating the receiving transducer from the transmitting electrodes removes the received signal, in time, from the cross-talk in the instrumentation during the transmit pulse. In the instrument decribed, fluid separates the transmitting electrodes and the receiving transducer. However, as long as the receive transducer samples the sound generated in the liquid, it may have a solid or a liquid separating it from the source of sound generation.

DETAILED DESCRIPTION OF THE INVENTION

Figure 1:
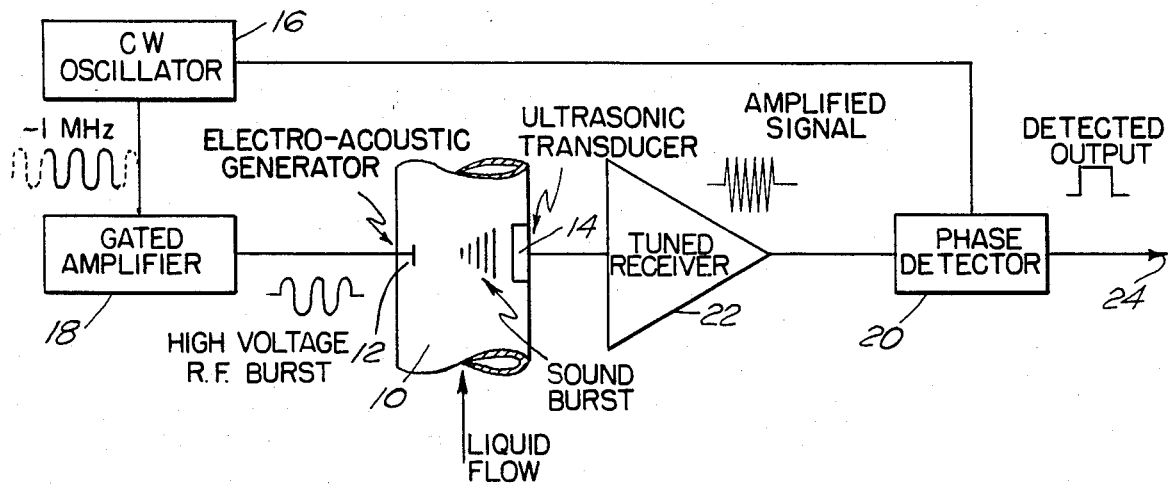
FIG. 1 is a schematic of one form of the apparatus of our invention.

In proceeding with the invention, we have discovered essentially that quantities of particles or emulsion droplets can be detected and measured in liquids by applying an alternating current electrical potential to an electrode configuration which is in contact with the liquid. This electrode configuration generates sound in directions determined to some extent by its geometry. After the fluid is energized in this manner, the amplitude of the signal at a distance spaced from the electrode configuration is received and observed. To achieve this type of result, an apparatus such as seen in FIG. 1 may be utilized, in which there is seen a section of a pipe 10 which may be considered to be in a process stream, or alternatively could be cylindrical container in a static or non-flowing mode. An acoustic generator consisting of an electrode configuration 12 is mounted in one part of the pipe wall with the electrodes in contact with liquid in the pipe, and opposite the generator 12 is a conventional acoustic transducer 14. To energize the system, a continuous wave oscillator 16 that may generate a frequency between 0.5 to 5.0 MHz is fed into a gated amplifier 18 and simultaneously into a phase detector 20. The output of the gated amplifier 18 is effectively a burst of several cycles, generally at several hundred volts amplitude which is fed to the electro-acoustic transducer 12. Preferably techniques are utilized to monitor the amplitude of the electrical signal at electro-acoustic generator 12 so that a constant amplitude electrical signal is applied to this generator regardless of the electrical conductivity of the liquid.

Figure 3:
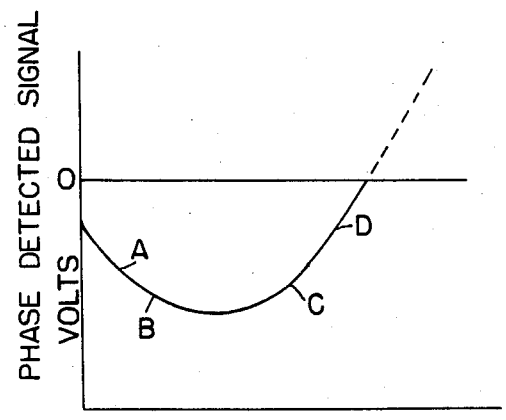
FIG. 3 is a graph illustrating the effect of using the apparatus.

The energy which is received at the ultrasonic transducer 14 has its output fed to a tuned receiver 22 and thence to the phase or amplitude sensitive detector 20, where essentially the RF carrier from the CW oscillator is stripped and the resultant is seen at the output at 24, which can be fed to conventional monitoring devices such as oscilloscopes, recorders and the like. In addition, inasmuch as the output of the oscillator 16 is fed to the phase detector 20, the phase difference of the oscillator 16 to that of the received signal may also be monitored. Essentially, the relative phase of the wave received at the transducer 14 depends on the distance between the transmitter 12 and the transducer 14, the sound speed in the liquid medium and the sign of the net electrical charge on the particle or emulsion droplets. If a change in the phase of the electrical signal occurs, as into the dotted line area of FIG. 3, at a fixed colloid or emulsion droplet concentration and at a constant temperature, it will be because of a change of sign of charge on the particles inasmuch as the distance between the generator and the transducer always remains constant.

A successful version of an electrode assembly pair electro-acoustical generator configuration is seen in the drawings. Here a pipe wall 11 which is of some metalic material will act as one electrode or ground plane and through this pipe wall, a hole is drilled as at 26. Preferably the inner surface of the pipe is made flat as with a back spot facing tool, and into this hole and resting on the flattened portion is mounted a circular cylindrical electrical insulator part 30 which has a dimension d which is one-half of a wave length or odd integer multiples of $\lambda/2$ of the sound that will be generated. Within the cylindrical portion is mounted a second electrode that will be separated from the ground plane by $(2n+1)$ $\lambda/2$ and when this electrode is positive with respect to the pipe wall, electric field lines will originate here and will terminate on the pipe wall.

In essence what is happening is that the sound pulse will be received at a certain number of micro-seconds after the transmitted pulse, depending upon the amount of time it takes the sound signal to traverse the pipe. This signal will be seen at the output of the phase detector and will be either positive or negative, depending upon the signal of the charge on the particles. There are several advantages of generating the sound with a pulsed alternating electric field as opposed to detecting sound by observing an oscillating electric field. The first advantage arises from our ability to maintain a constant amplitude electric field between the electrodes. This compensates for changes in conductivity of the fluid. No such compensating method is known for the inverse process. The second advantage results from the fact that it is relatively easy to produce a large electric field in the fluid and the process of detecting low level ultrasound is well known. Optimizing a receiving electrode assembly for use in a fluid with widely changing electrical characteristics is much more difficult, if not impossible. The electro-acoustical generator 12 which causes the charge displacement in the liquid, can have a number of configurations, but it must be realized that in order to properly energize the ions of the solution, the spacing (length d in drawings) between the electrodes should be effectively one-half wave length or odd integer multiples of half wave length for the frequency of the supplied energy.

Figure 2:
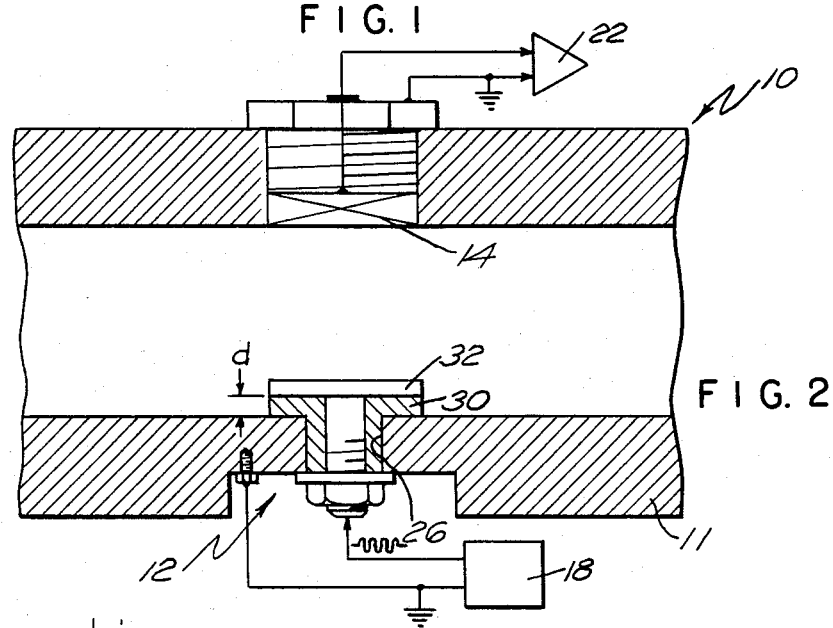
FIG. 2 is a cross-sectional view of one form of the transmitting electrode pair/receiving piezoelectric transducer configuration.
Figure 4:
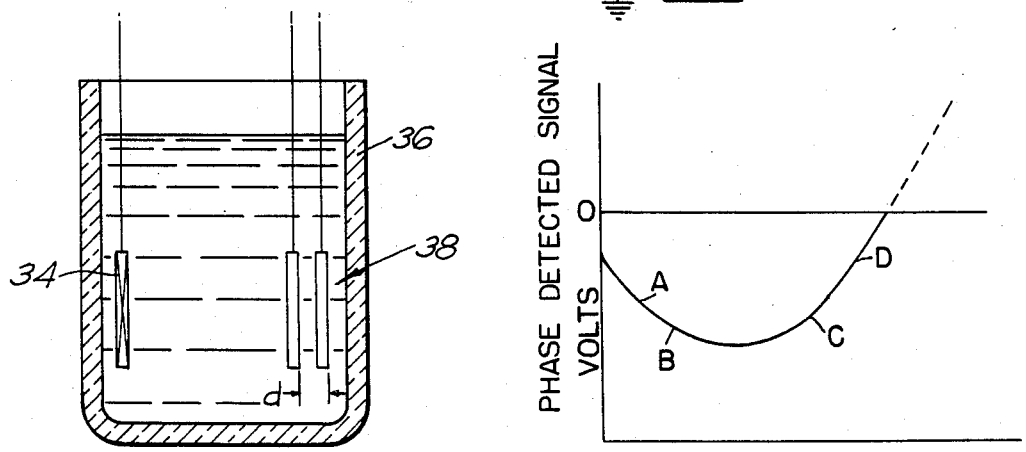
FIG. 4 is a cross-sectional view of another form of the transmitting electrode pair/receiving piezoelectric transducer configuration.

An example of how the apparatus is used in the laboratory situation will now be given. In many instances, it is desired to know how much dispersant chemical, such as a quaternary amine, is required to be incorporated into a given slurry such as $CaCO_3$ in order for it to be stabilized against flocculation and settling. The experimenter thus puts into a test chamber 36 in the form of a vessel (see FIG. 4), a quantity of slurry under study. The vessel is fitted with an electrode pair 38 which is energized. A conventional receiver transducer 34 is spaced from the electric pair. An initial output signal 24 is obtained from the slurry. For maximum slurry stability the output signal should be made as large as possible. This requirement means that for a given particle concentration each particle has maximum amount of possible electrical charge placed on it. Now, if the addition of small quantities, in parts per million, of dispersant chemicals result in increase in signal amplitude, as for example from A to B in FIG. 3, the slurry can be further stabilized by additional doses of the chemical. If on the other hand the addition of small quantity of dispersant decreases the signal size, as for example from C to D in FIG. 3, implying a decrease in slurry particle charge, this may indicate to the experimenter that the wrong type of chemical is being used or that sufficient amounts of the right kind of chemical has already been used. Quantitative results in terms of part per million surfactant at a given slurry concentration for optimal dispersal can be obtained. It is clear that similar results can be obtained with this device in the on-line, flow-through configuration, as in FIG. 2, the only difference being that chemical additions are made at some upstream point and adequate time, determined by flow rate, must be given for proper mixing and reacting.

In many other instances this apparatus will be used to determine when, for a given slurry concentration, the output signal 24 is a minimum, preferably zero. An on-line situation occurs for example, in waste-water treatment and pulp and paper plants where the intent is to make the charges on the individual slurry particles as small as possible so that they will naturally stick together. In this condition, only attractive van der Waals forces will be operative. This state is achieved by addition of suitable chemicals called flocculants. One of the goals in these studies is to determine from a large class of possible available flocculants, that chemical which will be most economically efficient to use. Similar results will be achieved with emulsions.

In the above discussions, we have been talking about the addition of suitable chemicals such as flocculants and dispersants so as to achieve an optimum result or a particular result, which chemicals in essence are charge modifiers since the net electrical charge of the particles or droplets is being changed or modified as the case might be by creating a charge displacement in the solution and monitoring the particle's or droplet's charge.

We claim:

1. A method of measuring electro-kinetic properties of charged particles dispersed in a liquid medium which method comprises the steps of positioning two electrodes to contact the liquid medium, energizing the electrodes with an alternating electrical potential to cause a charge separation between the surfaces of the dispersed particles and the charge layers that surround the particles in the liquid medium and thereby to generate an acoustic signal, spacing an acoustic transducer from the electrodes for detecting the acoustic signal, and measuring the amplitude of the detected signal, the amplitude of the detected signal being a function of the electro-kinetic properties of the particles present in the liquid medium, the number of particles per unit volume and the amplitude of the excitation potential on the electrodes.

2. A method according to claim 1 including the step of positioning the electrodes directly in a section of a conduit through which a dispersion is flowing.

3. A method according to claim 1 including the further step of controlling the amplitude of the energizing alternating potential in the presence of changes in the electrical conductivity of the liquid medium.

4. A method according to claim 1 comprising the further step of comparing the phase of the detected signal with the phase of the applied electrical potential in order to determine the polarity of the charge on the particles.

5. A method according to claim 1 further comprising the step of adding a small quantity of a charge modifying chemical to the liquid medium and again measuring the amplitude of the received signal to assess the effect of the addition.

6. An apparatus for measuring the electro-kinetic properties of a particle dispersion in a flowing medium which apparatus comprises a source of alternating electrical potential, a conduit, an electrode assembly located in the wall of the conduit and having a ground plane and a conductor separated from the ground plane in the conduit by an insulator having a thickness of $(2n+1)\lambda/2$ and located to contact the liquid medium, and a receiving acoustic transducer also in contact with the liquid medium.

7. An apparatus according to claim 6 wherein a gated amplifier is placed between the source and the generator.

8. An apparatus according to claim 6 further comprising a receiver coupled to the transducer and tuned to the source frequency for observing the received signal.

9. An apparatus according to claim 6 further comprising a phase detector for determining the phase of the received signal relative to the phase of the applied alternating electrical potential.

* * * * *